(12) United States Patent
    Hadlock et al.

(10) Patent No.: US 8,577,917 B2
(45) Date of Patent: Nov. 5, 2013

(54) SYSTEMS AND METHODS FOR IMPROVING CACHE HIT SUCCESS RATE USING A SPLIT CACHE

(75) Inventors: Wade Curtis Hadlock, Murray, UT (US); Scott Price, Salt Lake City, UT (US)

(73) Assignees: General Electric Company, Schenectady, NY (US); IHC Health Services Inc., Salt Lake City, UT (US)

( * ) Notice: Subject to any disclaimer, the term of this patent is extended or adjusted under 35 U.S.C. 154(b) by 122 days.

(21) Appl. No.: 13/205,429

(22) Filed: Aug. 8, 2011

(65) Prior Publication Data

US 2013/0041914 A1   Feb. 14, 2013

(51) Int. Cl.
    *G06F 17/30* (2006.01)
(52) U.S. Cl.
    USPC ............................. 707/770; 707/769; 709/223
(58) Field of Classification Search
    USPC ................................... 707/769, 770; 709/723
    See application file for complete search history.

(56) References Cited

U.S. PATENT DOCUMENTS

| 7,376,790 B2 | 5/2008 | Lango et al. |
| 2008/0065718 A1* | 3/2008 | Todd et al. ................... 709/203 |
| 2011/0035553 A1* | 2/2011 | Shepstone et al. ............ 711/135 |

* cited by examiner

*Primary Examiner* — Etienne Leroux
*Assistant Examiner* — Cindy Nguyen
(74) *Attorney, Agent, or Firm* — Hanley, Flight and Zimmerman, LLC

(57) ABSTRACT

Certain examples provide a clinical cache system for retrieval of varying clinical content. The system includes an input to include a request for a content item and one or more parameters associated with the content item. The system includes a metadata cache to store one or more sets of metadata representing parameters associated with one or more content items. The one or more sets of metadata in the metadata cache are used to identify and distinguish one or more content items with respect to the request. The system includes a content cache to store one or more content items. The one or more content items are searchable based on associated metadata. The metadata cache and the content cache facilitate the request by first querying the metadata cache and then querying the content cache based on a result of the metadata cache query.

20 Claims, 11 Drawing Sheets

SYSTEMS AND METHODS FOR IMPROVING CACHE HIT SUCCESS RATE USING A SPLIT CACHE

FIELD OF THE DISCLOSURE

The present disclosure relates generally to healthcare information systems and, more particularly, to methods and apparatus for content-driven systems and methods.

BACKGROUND

Healthcare environments, such as hospitals and clinics, typically include information systems (e.g., electronic medical record (EMR) systems, lab information systems, outpatient and inpatient systems, hospital information systems (HIS), radiology information systems (RIS), storage systems, picture archiving and communication systems (PACS), etc.) to manage clinical information such as, for example, patient medical histories, imaging data, test results, diagnosis information, management information, financial information, and/or scheduling information. These healthcare information systems are used to implement different types of workflows in which clinical information is generated, updated, augmented, and/or otherwise processed for one or more purposes.

A simple service that uses a cache to return data typically receives an identifier, checks to see if the identifier is in the cache and, if found, returns the data from the cache. If the identifier is not found in the cache, the service retrieves the data from another service, file system, or database. The service then stores the data in the cache and returns the data. The next time the data is needed, a call to another service is not necessary.

For this cache operation to work, each identifier must uniquely identify one item in the cache. If the data in the cache can be represented by more than one identifier, then the cache either needs to store the data multiple times under each identifier, or store all the identifiers for each data item.

BRIEF SUMMARY

Certain examples provide a clinical split cache system for retrieval of varying clinical content. The system includes an input to include a request for a content item and one or more parameters associated with the content item. The system includes a metadata cache to store one or more sets of metadata representing parameters associated with one or more content items. The one or more sets of metadata in the metadata cache are to be used to identify and distinguish one or more content items with respect to the request. The system includes a content cache to store one or more content items. The one or more content items are to be searchable based on associated metadata. The metadata cache and the content cache are to facilitate the request by first querying the metadata cache and then querying the content cache based on a result of the metadata cache query. The system includes an output of the requested content item.

Certain examples provide a tangible computer-readable storage medium including a set of instructions, which when executed by a processor, implement a clinical split cache system for retrieval of varying clinical content. The system includes an input to include a request for a content item and one or more parameters associated with the content item. The system includes a metadata cache to store one or more sets of metadata representing parameters associated with one or more content items. The one or more sets of metadata in the metadata cache are to be used to identify and distinguish one or more content items with respect to the request. The system includes a content cache to store one or more content items. The one or more content items are to be searchable based on associated metadata. The metadata cache and the content cache are to facilitate the request by first querying the metadata cache and then querying the content cache based on a result of the metadata cache query. The system includes an output of the requested content item.

Certain examples provide a method of retrieving varying clinical content. The method includes receiving a request for a content item and one or more parameters associated with the content item. The method includes querying a metadata cache based on the one or more parameters associated with the content item and a content item identifier to identify metadata associated with the requested content item. The metadata cache stores one or more sets of metadata representing parameters associated with one or more content items. The one or more sets of metadata in the metadata cache are to be used to identify and distinguish one or more content items with respect to the request. The method includes querying a content cache using the content item identifier and the metadata associated with the request content item. The content cache is to store one or more content items. The one or more content items are searchable based on associated metadata. The metadata cache and the content cache are to facilitate the request by first querying the metadata cache and then querying the content cache based on a result of the metadata cache query. The method includes providing an output of the requested content item.

Figure 1:
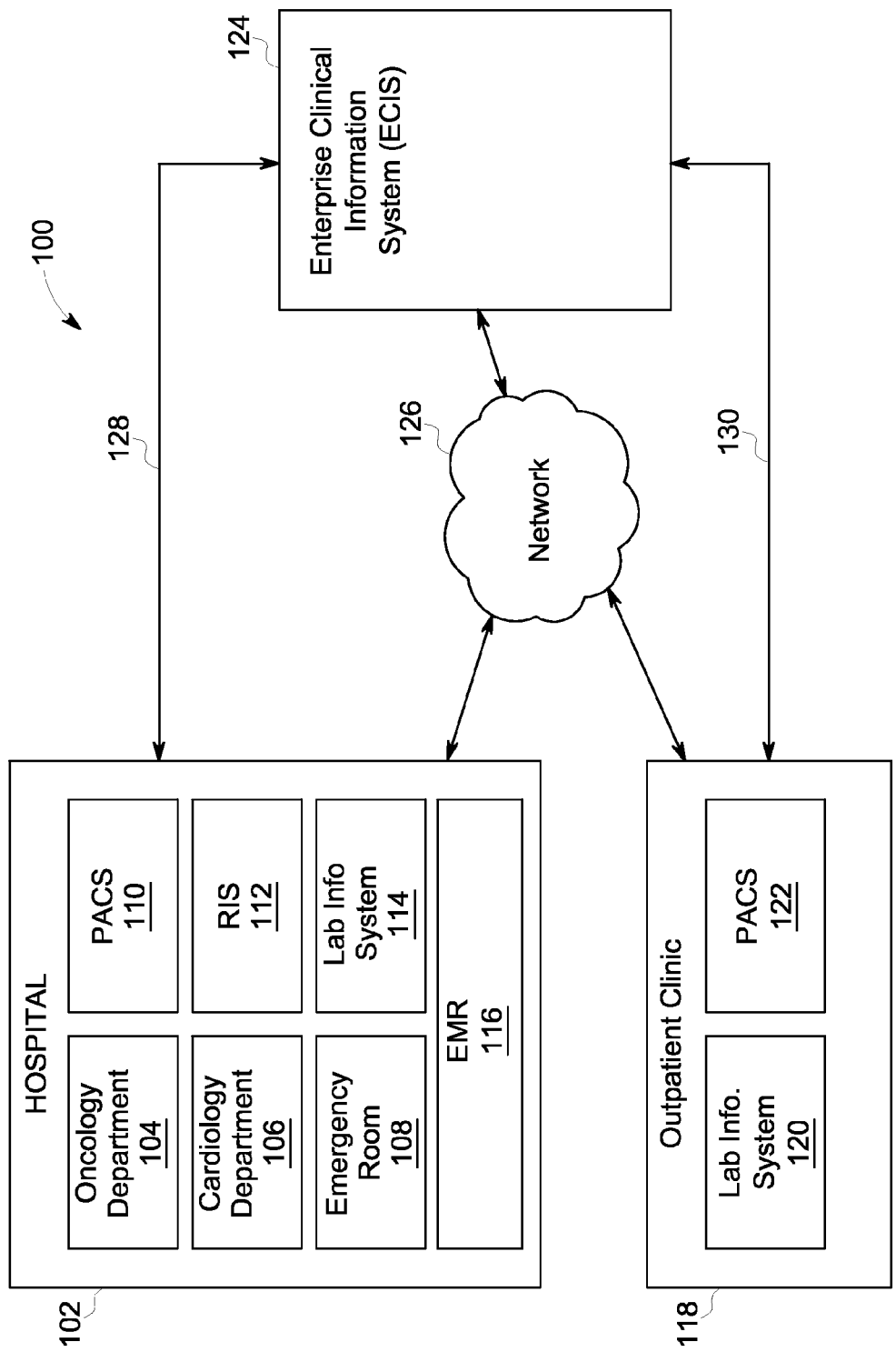
FIG. 1 is a block diagram of an example healthcare environment in which the example methods, apparatus, systems and/or articles of manufacture described herein to organize healthcare information may be implemented.

The foregoing summary, as well as the following detailed description of certain examples of the present invention, will be better understood when read in conjunction with the appended drawings. For the purpose of illustrating the invention, certain examples are shown in the drawings. It should be understood, however, that the present invention is not limited to the arrangements and instrumentality shown in the attached drawings.

DETAILED DESCRIPTION

Although the following discloses example methods, apparatus, systems, and articles of manufacture including, among other components, firmware and/or software executed on hardware, it should be noted that such methods, apparatus, systems, and/or articles of manufacture are merely illustrative and should not be considered as limiting. For example, it is contemplated that any or all of these firmware, hardware, and/or software components could be embodied exclusively in hardware, exclusively in software, exclusively in firmware, or in any combination of hardware, software, and/or firmware. Accordingly, while the following describes example methods, apparatus, systems, and/or articles of manufacture, the examples provided are not the only way(s) to implement such methods, apparatus, systems, and/or articles of manufacture.

Entities of healthcare enterprises operate according to a plurality of clinical workflows. Clinical workflows are typically defined to include one or more steps or actions to be taken in response to one or more events and/or according to a schedule. Events may include receiving a healthcare message associated with one or more aspects of a clinical record, opening a record(s) for new patient(s), receiving a transferred patient, and/or any other instance and/or situation that requires or dictates responsive action or processing. The actions or steps of a clinical workflow may include placing an order for one or more clinical tests, scheduling a procedure, requesting certain information to supplement a received healthcare record, retrieving additional information associated with a patient, providing instructions to a patient and/or a healthcare practitioner associated with the treatment of the patient, and/or any other action useful in processing healthcare information. The defined clinical workflows can include manual actions or steps to be taken by, for example, an administrator or practitioner, electronic actions or steps to be taken by a system or device, and/or a combination of manual and electronic action(s) or step(s). While one entity of a healthcare enterprise may define a clinical workflow for a certain event in a first manner, a second entity of the healthcare enterprise may define a clinical workflow of that event in a second, different manner. In other words, different healthcare entities may treat or respond to the same event or circumstance in different fashions. Differences in workflow approaches may arise from varying preferences, capabilities, requirements or obligations, standards, protocols, etc. among the different healthcare entities.

However, the entities of a healthcare enterprise and/or entities from separate healthcare enterprises sometimes operate within a broader, interdependent information system, which hinder the ability of entities to customize clinical workflows. For example, the information system to which a healthcare entity belongs may place restrictions on changes to workflow applications or programs. Moreover, because some healthcare entities operate using systems, programs, devices, etc. from varying manufactures, software providers, etc., a lack of interoperability between the systems, programs, devices, etc. of each healthcare entity prohibits many customizations from realization. As a consequence of these example factors as well as additional or alternative factors, healthcare entities that desire customized clinical workflows are typically required to request such customizations from the manufactures, software providers, etc. Furthermore, for such customizations to implemented or integrated into a healthcare information system, a wide range of system-interrupting updates or re-releases occur within the information systems.

Certain examples provide a clinical knowledge platform that enables healthcare institutions to improve performance, reduce cost, touch more people, and deliver better quality globally. In certain examples, the clinical knowledge platform enables healthcare delivery organizations to improve performance against their quality targets, resulting in better patient care at a low, appropriate cost.

Certain examples facilitate better control over data. For example, certain example systems and methods enable care providers to access real-time patient information from existing healthcare information technology (IT) systems together in one location and compare this information against evidence-based best practices.

Certain examples facilitate better control over process. For example, certain example systems and methods provide condition- and role-specific patient views enable a user to prioritize and coordinate care efforts with an institution's agreed upon practice standards and to more effectively apply resources.

Certain examples facilitate better control over outcomes. For example, certain example systems and methods provide patient dashboards that highlight variations from desired practice standards and enable care providers to identify most critical measures within the context of performance-based care.

Certain examples leverage existing IT investments to standardize and centralize data across an organization. In certain examples, this includes accessing multiple systems from a single location, while allowing greater data consistency across the systems and users.

In certain examples, an advanced Service-Oriented Architecture (SOA) with a modern technology stack helps provide robust interoperability, reliability, and performance. The example SOA includes a three-fold interoperability strategy including a central repository (e.g., a central repository built from Health Level Seven (HL7) transactions), services for working in federated environments, and visual integration with third-party applications. Certain examples provide portable content enabling plug'n play content exchange among healthcare organizations. A standardized vocabulary using common standards (e.g., LOINC, SNOMED CT, RxNorm, FDB, ICD-9, ICD-10, etc.) is used for interoperability, for example. Certain examples provide an intuitive user interface to help minimize end-user training. Certain examples facilitate user-initiated launching of third-party applications directly from a desktop interface to help provide a seamless workflow by sharing user, patient, and/or other contexts. Certain examples provide real-time (or at least substantially real time assuming some system delay) patient data from one or more IT systems and facilitate comparison(s) against evidence-based best practices. Certain examples provide one or more dashboards for specific sets of patients. Dashboard(s) can be based on condition, role, and/or other criteria to indicate variation(s) from a desired practice, for example.

Generally, the example methods, apparatus, systems, and/or articles of manufacture disclosed herein enable healthcare entities of an enterprise clinical information system (ECIS) to dynamically customize one or more clinical workflows. Among other functions and/or benefits, the ECIS supports healthcare practitioners in decision making processes by aggregating healthcare information across disparate enterprises and/or entities thereof and referencing collection(s) of data (e.g., guidelines, recommendations related treatment and/or diagnosis, studies, histories, etc.) to automatically generate supportive information to be communicated to one or more healthcare practitioners related to the aggregated healthcare information. While each entity operates in connection with the ECIS that is administered by a provider thereof, the examples disclosed herein enable each entity of operating in connection with the ECIS to originate and/or modify one or more clinical workflows without relying on the provider of the ECIS to do so on behalf of the entity. In other words, although a healthcare entity is part of the ECIS and exchanges data with and via the ECIS, that entity can independently create and/or manage its clinical workflows using the examples disclosed herein. Furthermore, the examples disclosed herein enable entities of the ECIS to deploy or initiate the customized workflows without having to reboot or significantly interrupt the ECIS and/or the other components, workflows, etc., thereof. The example methods, apparatus, systems, and/or articles of manufacture disclosed herein and the advantages and/or benefits thereof are described in greater detail below in connection with the figures.

FIG. 1 is a block diagram of an example healthcare environment 100 in which the example methods, apparatus, systems, and/or articles of manufacture disclosed herein for clinical content-based healthcare may be implemented. The example healthcare environment 100 of FIG. 1 includes a first hospital 102 having a plurality of entities operating within and/or in association with the first hospital 102. In the illustrated example, the entities of the first hospital 102 include an oncology department 104, a cardiology department 106, an emergency room system 108, a picture archiving and communication system (PACS) 110, a radiology information system (RIS) 112, and a laboratory information system (LIS) 114. The oncology department 104 includes cancer-related healthcare practitioners, staff and the devices or systems that support oncology practices and treatments. Similarly, the cardiology department 106 includes cardiology-related healthcare practitioners, staff and the devices and/or systems that support cardiology practices and treatments. Notably, the example oncology department 104 of FIG. 1 has specifically designed clinical workflows to be executed in response to certain events and/or according to a schedule. At the same time, the example cardiology department 106 of FIG. 1 has specifically designed clinical workflows to be executed in response to certain events and/or according to a schedule that differ from the clinical workflows of the example oncology department 104 of FIG. 1. For example, the oncology department 104 may execute a first set of actions in response to receiving a Healthcare Level 7 (HL7) admission-discharge-transfer (ADT) message, while the cardiology department 106 executes a second set of actions different from the first set of actions in response to receiving a HL7 ADT message. Such differences may also exist between the emergency room 108, the PACS 110, the RIS 112 and/or the accounting services 114.

Briefly, the emergency room system 108 manages information related to the emergency care of patients presenting at an emergency room of the hospital 102, such as admission information, observations from emergency examinations of patients, treatments provided in the emergency room setting, etc. The PACS 110 stores medical images (e.g., x-rays, scans, three-dimensional renderings, etc.) as, for example, digital images in a database or registry. Images are stored in the PACS 110 by healthcare practitioners (e.g., imaging technicians, physicians, radiologists) after a medical imaging of a patient and/or are automatically transmitted from medical imaging devices to the PACS 110 for storage. The RIS 112 stores data related to radiology practices such as, for example, radiology reports, messages, warnings, alerts, patient scheduling information, patient demographic data, patient tracking information, and/or physician and patient status monitors, as well as enables exam order entry (e.g., ordering an x-ray of a patient) and image and film tracking (e.g., tracking identities of one or more people that have checked out a film). The lab information system 114 stores clinical information such as lab results, test scheduling information, corresponding practitioner(s), and/or other information related to the operation(s) of one or more labs at the corresponding healthcare facility. While example types of information are described above as being stored in certain elements of the hospital 102, different types of healthcare data may be stored in one or more of the entities 104-114, as the entities 104-114 and the information listed above is included herein as non-limiting examples. Further, the information stored in entities 104-114 may overlap and/or be combined into one or more of the entities 104-114. Each of the example entities 104-114 of FIG. 1 interacts with an electronic medical record (EMR) system 116. Generally, the EMR 116 stores electronic copies of healthcare records associated with, for example, the hospital 102 and the entities 104-114 thereof.

The example healthcare environment 100 of FIG. 1 also includes an outpatient clinic 118 as an example of another healthcare enterprise. The example outpatient clinic 118 of FIG. 1 includes a lab information system 120 and a PACS 122 that operate similarly to the corresponding entities of the example hospital 102. The lab information system 120 and the PACS 122 of the example outpatient clinic 118 operate according to specifically designed clinical workflows that differ between each other and the clinical workflows of the entities 104-114 of the hospital 102. Thus, differences in clinical workflows can exist between the entities of a healthcare enterprise and between healthcare enterprises in general.

In the illustrated example of FIG. 1, the hospital 102 and the outpatient clinic 118 are in communication with an ECIS 124 via a network 126, which may be implemented by, for example, a wireless or wired Wide Area Network (WAN) such as a private network or the Internet, an intranet, a virtual private network, a wired or wireless Local Area Network, etc. More generally, any of the coupling(s) described herein may be via a network. Additionally or alternatively, the example hospital 102 and/or the example outpatient clinic 118 are in communication with the example ECIS 124 via direct or dedicated transmission mediums 128 and 130.

Generally, the ECIS 124 supports healthcare information processing implemented by systems, devices, applications, etc. of healthcare enterprises, such as the hospital 102 and the outpatient clinic 118. The ECIS 124 is capable of processing healthcare messages from different entities of healthcare enterprises (e.g., the entities 104-114 of the hospital 102) that may generate, process and/or transmit the healthcare messages differently and/or using different formats, protocols, policies, terminology, etc. when generating, processing, and/or transmitting the healthcare messages. Moreover, the example ECIS 124 of FIG. 1 supports healthcare practitioners in decision making processes by aggregating healthcare information across disparate enterprises and/or entities thereof and referencing collection(s) of data to automatically generate suggestive and/or definitive data for communication to one or more healthcare practitioners related to the aggregated healthcare information.

Certain examples provide a library of standardized clinical content and proven best practices. Over time, this "library" of content may expand as healthcare organizations add to their own content modules. Because the content is standardized it can be shared and leveraged among organizations using the library and associated clinical knowledge platform. The library and platform help enable organizations to share best practice content. Thus, certain examples provide a clinical knowledge platform that enables healthcare delivery organizations to improve performance against their quality targets.

In certain examples, a quality dashboard application enables creation of one or more dashboards based on the data/content most relevant to an organization at a given period of time. A clinical knowledge platform brings together real-time patient data from existing IT systems within an organization and allows for the comparison of this data against evidence-based best practices. The example quality dashboard application leverages the platform to enable personalized "Quality Dashboards" to be created for specific sets of patients, based on condition, role, and/or other criteria. Variations from desired practice will be highlighted on each dashboard, enabling care providers to ensure better clinical outcomes and enrich patient care.

Figure 2:
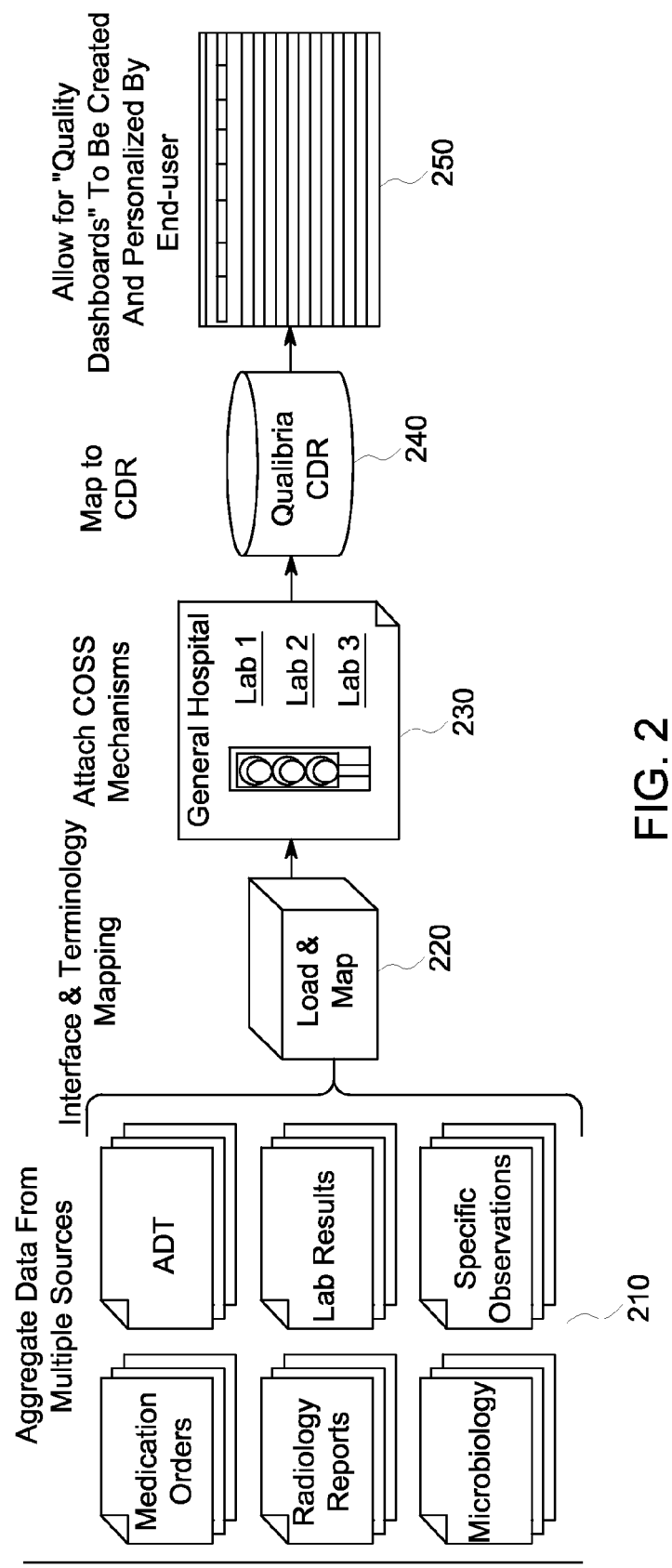
FIG. 2 illustrates an example clinical knowledge system providing an aggregation of data from multiple sources.

In this example, the clinical knowledge platform aggregates data from an organization's existing IT solutions. These can be solutions from the same and/or different manufacturer and/or provider. For example, as long as there is an HL7 or Web Services feed, the clinical knowledge platform can utilize the data from an existing solution. The existing IT solution(s) will continue to operate as they always have, and an organization can continue to use these solutions separate from the clinical knowledge platform if they so desire. However, the clinical knowledge platform and associated application(s) and/or workflow(s) can help to put organizations in greater control of their data by aggregating as much data from disparate IT solutions as possible. FIG. 2 illustrates an example clinical knowledge system 200 providing an aggregation 210 of data from multiple sources. Aggregated data may include, for example, medication orders, radiology reports, microbiology, admit/discharge/transfer (ADT) message, lab results, specific observations, electronic medical record (EMR) data, etc.

As the different data sources are pulled into a central data repository, content standardization occurs. It is this "standardization" that enables content from different IT sources to be used together. For example, as shown in FIG. 2, an interface 220 provides terminology mapping and standardization to the aggregated data.

After the content is standardized, clinical decision support mechanisms can be tied to the content (as illustrated, for example, by the clinical decision support 230 of the system 200 of FIG. 2). The data and associated clinical decision support are then stored in a clinical data repository (CDR), such as CDR 240 of the example system 200. By combining the aggregated and standardized data with clinical decision support rules and alerts, the clinical knowledge platform may provide end-users with an understanding of important elements to which they should pay attention (and take action on) within the larger set of data they are considering when caring for a patient.

Combined data and clinical decision support mechanisms create valuable content that, when arranged properly, may be used to improve the quality of care provided. Organizations can elect to use the application(s) that are provided as a part of the example clinical knowledge platform and/or may choose to build their own clinical application(s) on the platform. The open architecture nature of the platform empowers organizations to build their own vision, rather than base their vision on the static/hard coded nature of traditional IT solutions.

In certain examples, "Quality Dashboards" created via an example application display data via columns and rows in addition to individual patient "inspector" views. For example, the system 200 shown in FIG. 2 provides one or quality dashboards 250 to be created and personalized by an end user. The flexible nature of this dashboard application empowers organizations to create dashboards of the aggregated data based on their needs at a given period of time. The organization may determine what data elements they would like to include on each dashboard and, without significant IT resources, create a dashboard that reflects their vision. In addition, organizations can determine where on the dashboard they would like the information to be displayed and further adjust the view of the content via features such as "bolding" font, etc. When data is added to each dashboard, clinical decision support mechanisms attached to this data are displayed on the dashboard as well. For example, content related to treating a patient based on a particular use case may be included on a quality dashboard, along with alerts and notifications to indicate to end-users when desired outcomes are varying from defined clinical standards. Thus, organizations can create dashboards based on their own idea of "best practice" care for a given disease state.

In certain examples, since combined content and best practices have been standardized, content from one organization using the clinical knowledge platform may be easily shared with other organizations utilizing the platform. In addition, because the content within platform-related applications is standardized in the same manner, upgrades to the example platform can occur efficiently across organizations. That represents a dramatic change from prior IT solutions which require unique IT upgrades because they are usually uniquely customized to each organization in which they are installed.

Generally, content is information and experience that may provide value for an audience. Any medium, such as the Internet, television, and audio CDs, may deliver content as value-adding components. Content represents the deliverable, such as a DVD movie, as opposed to the delivery mechanism, a DVD player. As long as content conforms to the media standard, any compatible device can play it.

Content, as used herein, is the externalization or parameterization of "the instructions" that tell applications how to work. For example, content is a collection of externalized information that tells software, in conjunction with data, how to behave. In certain examples, a clinical knowledge platform takes in and executes content against data to render applications visually and behaviorally.

Content includes data read and interpreted by a program to define or modify presentation, behavior, and/or semantics of the program and/or of application data consumed by the program, for example. Content includes documents presented to a client by a program without modification, for example. Content may be created, stored, deployed, and/or retrieved independently of the creation and deployment of the program(s) consuming the data, for example. Content may be versionable to capture desired variation in program behavior and/or semantics, for example.

Classes of content may include configuration content, preferences content, reference content, application content, etc. Content types may combine behaviors of two or more classes, for example.

Software vendors take many different approaches to customization. At one extreme, some vendors write different software for each customer or allow customers to write software. At the other extreme, a vendor has the same software for each customer, and all customization occurs through creating or modifying content. In certain examples, the same software may be used for each customer, and customization is handled through content.

In healthcare, new laboratory tests, medications, and even diseases are constantly being discovered and introduced.

Structuring this as content, where underlying software does not need to change, helps accommodate and use updated information.

In certain examples, many different content types, such as form definitions, data models, database schema, etc., are accommodated. In certain examples, each content type may be used differently and involve a distinct authoring tool. Thus, in certain examples, content may refer to "a collection of the content instances for all content types," also called a content repository, knowledge repository, or knowledge assets. For example, a content instance is a specific member of a content type, such as a heart rate data model.

In certain examples, each content type is associated with a generic, extensible structure that content instances of the content type follows. An example clinical information system can specify content in an abstract way that does not presuppose a particular software implementation, for example. That is, another system, such as GE's Centricity Enterprise, may consume content from a knowledge repository, apply a different set of software, and achieve the same behaviors. Additionally, an abstract content definition can more easily transition to a new system. If one can extract content from a legacy system, a knowledge repository may be able to import and reuse it. Such a capability helps reduce a large barrier to change for potential customers.

Content can change with time. In an example, a current knowledge repository can handle any "old" data entered into a system under the auspices of an older knowledge repository. Occasionally, a question may arise where someone could ask, "What did Dr. Smith see at some past time?" Under these circumstances, a current definition of a particular display may not correctly reflect the situation at the time. An example CIS, unlike other systems, can bring back the old form for visualizing the data since all knowledge assets are versioned and retained.

Content may need to vary for different circumstances. For example, an MPV may differ between emergency department (ED) and labor and delivery settings. Each MPV has rows and columns of data specific to its setting. Context refers to being aware of and reacting distinctively to a location and other situational differences. For example, interpretation of a patient's low temperature can vary based on location. If it occurs in the recovery room after cardiopulmonary bypass with deliberate patient cooling, it means one thing. If the patient is in the ED after breaking through ice into a lake, it means something completely different. Context may vary based on user location, patient location, user role, and/or various other factors. In certain examples, content may be applied based on context.

Globalization is a process of adapting software so that it has no language references, before embedding capabilities to make it suitable for particular languages, regions, or countries. Having globalized it, a CIS may then translate it to other languages and cultures, called localization. Globalizing a software product involves creating content separate from the software. For example, embedded text (e.g., user messages), sort orders, radix characters, units of measure, data formats, currency, etc., may be removed and parameterized. References to languages, character sets, and fonts may also be removed, for example. In certain examples, while display representations may be local, terminology concepts are applied universally, making a rule, calculation, or other content based on one or more terminology concepts useable worldwide without modification.

Figure 3:
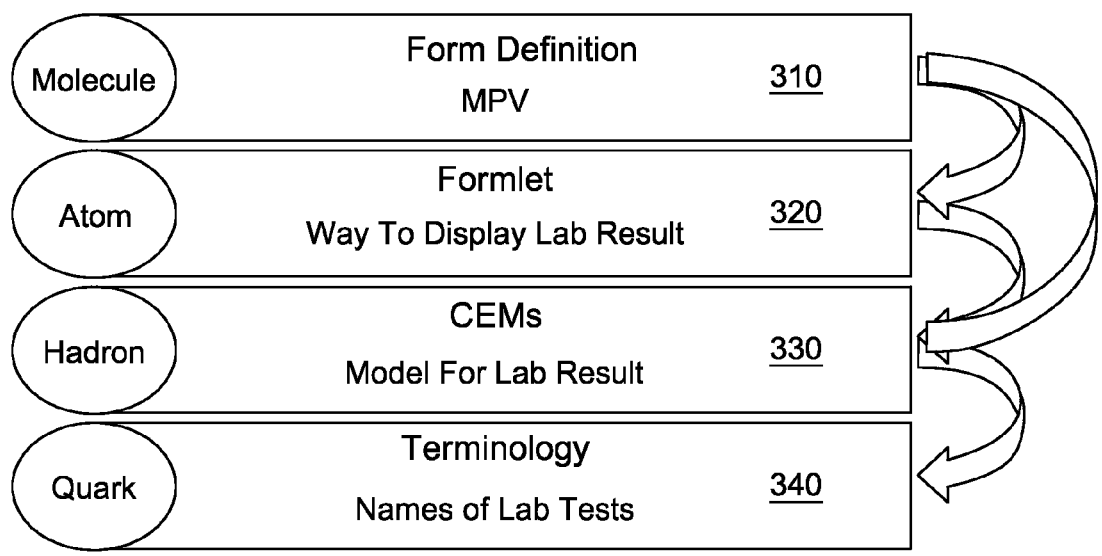
FIG. 3 illustrates an example interdependence of content types.

For example, FIG. 3 illustrates an example interdependence of content types. As shown in the example of FIG. 3, content is a set of interdependent building blocks. Content may be thought of as a hierarchy, with terminology 310 (e.g., names of lab tests) as a lowest level. Terminology 310 may be common and coded across a customer base. Clinical element models (CEMs) 320 govern structure and content of objects stored in a database and used by applications. A formlet 330 provides a way to display a particular content item (e.g., a way to display a particular lab result). A form definition 340 provides an application or view (e.g., a dashboard) of a collection of formlets (e.g., a multi-patient view (MPV) showing one or more lab results and/or other information). For example, if a particular MPV definition is moved from one customer to another, the MPV definition along with other content items on which the form definition depends are imported into the new customer's knowledge repository. Content items may include appropriate formlets, CEMs, and terminology, for example.

In certain examples, the Clinical Element Model presents a model for describing and representing detailed clinical information wherein each item of clinical information is defined using a detailed model of the information (that is, Detailed Clinical Models).

An example logical model to represent such a Detailed Clinical Model uses a two-layer data modeling approach in which the structure or representation of a clinical data object (that is, an instance of data) is separated from the definition of the information contained within the clinical data object (that is, a model defining the instance of data). This logical model defines the information in a Detailed Clinical Model as a set of constraints progressively limiting (and/or restricting) allowable data values in a Detailed Clinical Model until a specific clinical data item is defined.

In certain examples, a computer language, referred to as a Constraint Definition Language (CDL), is provided to define Detailed Clinical Models and constraints used to describe a specific clinical data item.

In certain examples, a detailed clinical model defines, at a granular level, the structure and content of a data element. For example, the detailed Clinical Model for "Heart Rate Measurement" dictates the data type of a heart rate measurement, and the valid physiologic range of a heart rate. It says that a "body location" is valid qualifying information about a heart rate measurement, but a "color" is not. It further decrees that the valid values for "body location" are terminology codes found in the "heart rate body location" value set. Moreover, it prescribes that a "resting heart rate" is an instance of "Heart Rate Measurement" where the value of "temporal context" is "resting", where "resting" is also a coded value. A detailed clinical model pulls the information together into a single, explicit, and computable form. The detailed clinical models or clinical element models (CEMs) govern the content and structure of all data objects stored in an example clinical database and used by applications, for example. In addition, CEMs are extensible, such that content authors may add new CEMs or attributes to existing CEMs without requiring major changes to database structures or software, for example.

In certain examples, shared or portable content is, in effect, "plug'n play". System administrators can add it (e.g., plug it into) to a system without any software changes, and the content behaves in the intended way and does not cause errors. The size or scope of shared content can range from a single term to an entire knowledge repository, for example. Shared content fundamentally changes an implementation paradigm and reduces a total system cost of ownership, for example.

Customers can change shared content. Customers can improve it or make it more suitable for their institutions. When customers do this, they leave the original definition intact, but clone it and keep their changed version in their "local" space, for example.

As described above, classes of content may include configuration content, preferences content, reference content, application content, etc. Configuration content is content that is modified infrequently and is concerned primarily with system behavior, for example. Examples of configuration content may include internet protocol (IP) address and port of clinical knowledge database, identifiers of terminals in systems, security access privileges, configuration files, etc. Configuration content may affect program semantics, for example. Configuration content is generally modified by system administrators and is often stored in the file system, for example.

Preference content is modified frequently and is concerned primarily with variation between users. Examples of preference content include display colors and fonts, default search parameters, screen layout, etc. Preference content rarely affects program semantics and is most commonly modified by individual users. While modified by users, the system generally distributes initial or default preference content.

In certain examples, distributed or default preference content behaves very similar to application content before modification by a user. Preference content may be context sensitive, transformed at deployment, etc. Preference content may include vocabulary concepts and pick-lists that are resolved when loading and retrieving just like other content types.

Reference content is documents that are presented without modification as part of the application. Reference content is often stored in formats that are opaque to a program (e.g., as a PDF, a Microsoft Word™ document, etc.). Reference content is generally not specific to or customized for a specific patient (e.g., instruction sheets, information sheets, policies and procedures, etc.). Reference content may be independent of program semantics and behavior. Reference content may be authored independently of a program. While not an element of a content drive system per se, reference content is often managed as content by a clinical knowledge system. Once reference content is modified for presentation to a specific user, the content starts behaving much more like patient data/documents. Reference content with the structure to enable modification starts behaving much more like application content.

Application content may be modified frequently or infrequently depending on use. Application content may be concerned primarily with application behavior and semantics. Applicant content may be generally specific to an application domain. Examples may include a flow sheet template, clinical element models, terminology, document templates that are modified and stored as patient data (e.g., hot text), etc. Terminology is application content but has behaviors distinct from other application content types and is managed (largely) independently of other application content, for example. Application data often affects program semantics and behavior. Application content may be authored at multiple levels in an organization or external to the organization, for example.

Application content may be implemented as a custom markup language, for example. Application content may be implemented as a domain specific language (DSL), for example. For example, data queries may be implemented using a frame definition language (FDL). Clinical element models may be implemented using a constraint definition language (CDL). Application content may be directly authored or imported as data into a content store (e.g., concepts in a vocabulary server), for example.

In certain examples, while patient data is transactional and often includes discrete data elements, application content is often structured, complex objects and often has associated metadata. In certain examples, metadata is data used to manage content, such as content identifier, version, name of author, access privilege, encryption certificate, etc. Metadata is not treated as content, for example. While patient data is owned by a patient and is part of a legal record, application content is not owned by a patient and is not part of a legal record. Application content may be published (e.g., is not transactional) and managed using a lifecycle.

Certain examples provide content-driven systems and processes that rely primarily on content to determine application behavior. An example system includes a reference platform that consumes, interprets, and/or executes content while remaining application neutral. An example system uses content that remains independent of an implementation of the reference platform to allow independent evolution of the platform and the application.

Figure 4:
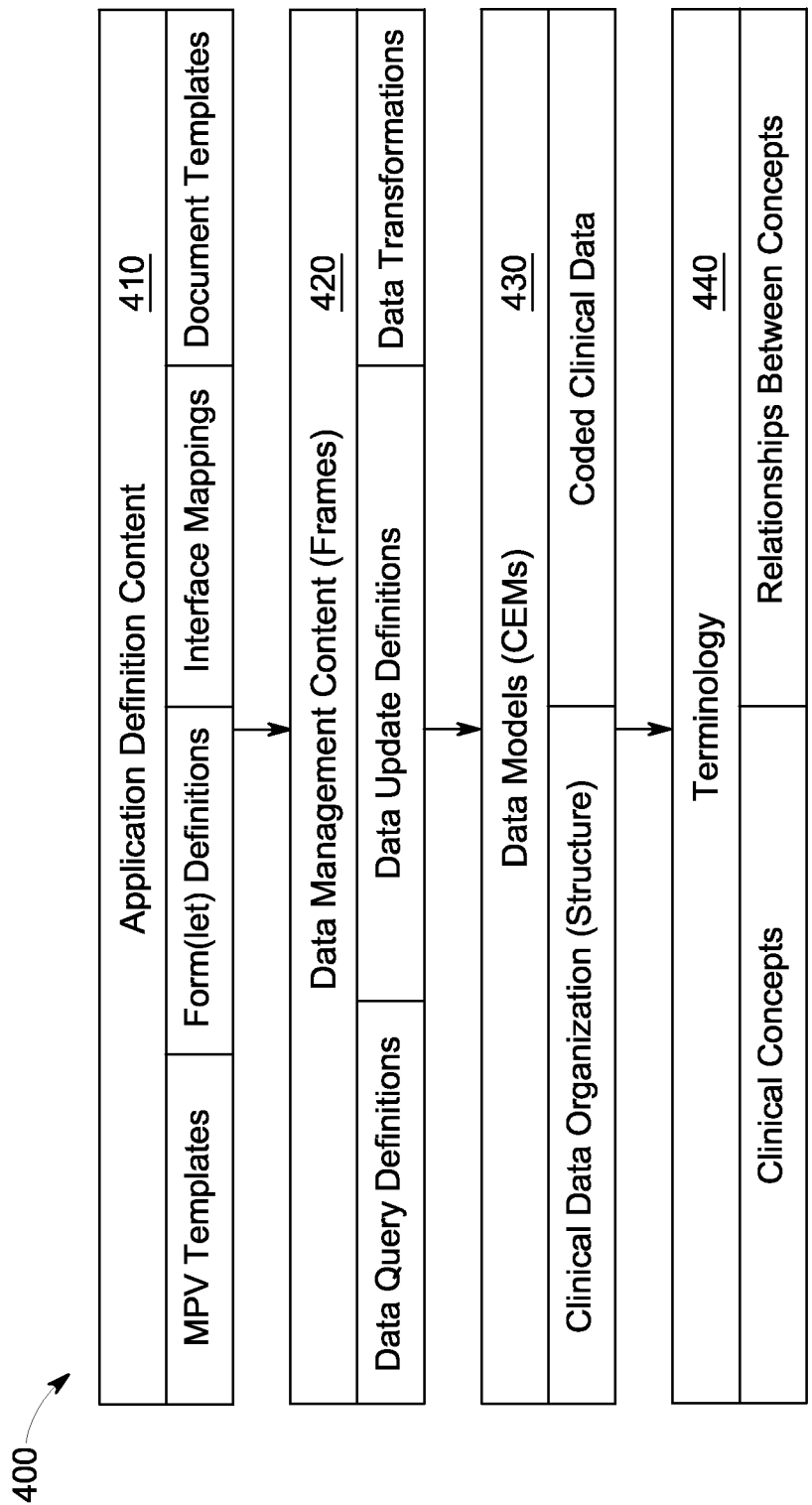
FIG. 4 illustrates an example hierarchy of content, associated data models, and terminology.

FIG. 4 illustrates an example hierarchy 400 of content, associated data models, and terminology. In certain examples, once one chooses content based data models, content-based queries and data management are also selected. Content based applications are also chosen. An integral terminology basis includes semantics of data defined in terminology content, for example. As shown in the example of FIG. 4, application definition content 410 (e.g., MPV templates, form(let) definitions, interface mappings, and/or document templates, etc.) relies on data management content (e.g., frames) 420 (e.g., data query definitions, data update definitions, and/or data transformations, etc.). The data management content 420 leverages data models (e.g., CEMs) 430, such as clinical data organization (e.g., structure) and/or coded clinical data, etc. The data models 430 are constructed based on a terminology 440 including clinical concepts and relationships between concepts, for example.

In certain examples, context refers to metadata attributes and/or labels that differentiate variations of a content item. For example, each variant of content item may be referred to as a context variant. Each variation of a content item has a specific set of context attributes (e.g., language, location, role, etc.). An algorithm or heuristic may select a desired variant when retrieving based on a current user's "context." This process may be referred to as context resolution.

Searching refers to examining the content item and/or associated metadata for matches independent of context. Searching can include context attributes to filter for specific context variants in the search. The difference is that a specific variant is not selected algorithmically or heuristically by the content system when searching. Using the "user" as a context attribute is one way to associate a content item with a specific user; similarly provider as a context variable could be used to associate an item with a group of users. Resolving context generally requires some heuristic to resolve ambiguity or conflicts among context variants (e.g., weighting or priority schemes, default rules, etc.). This leads to some ambiguity since changing/adding a context variant or changing the weights of context attribute may change the context resolution on another item in not always obvious ways (at least to a user).

In certain examples, a content item includes:

1. A root content item represented by a universally unique identifier (UUID). The root content item includes metadata only; no actual content is stored.

2. One or more context variants that represent variations of an implementation of the content item in different client contexts occur as children of the root content item.

3. Context variants may form trees of increasing context specialization (e.g., a context variant may have child variants).

4. Each context variant has a unique UUID as well as a relation to the root content item.

5. Each context variant maintains versions of that variant as changes are applied to the variant.

Figure 5:
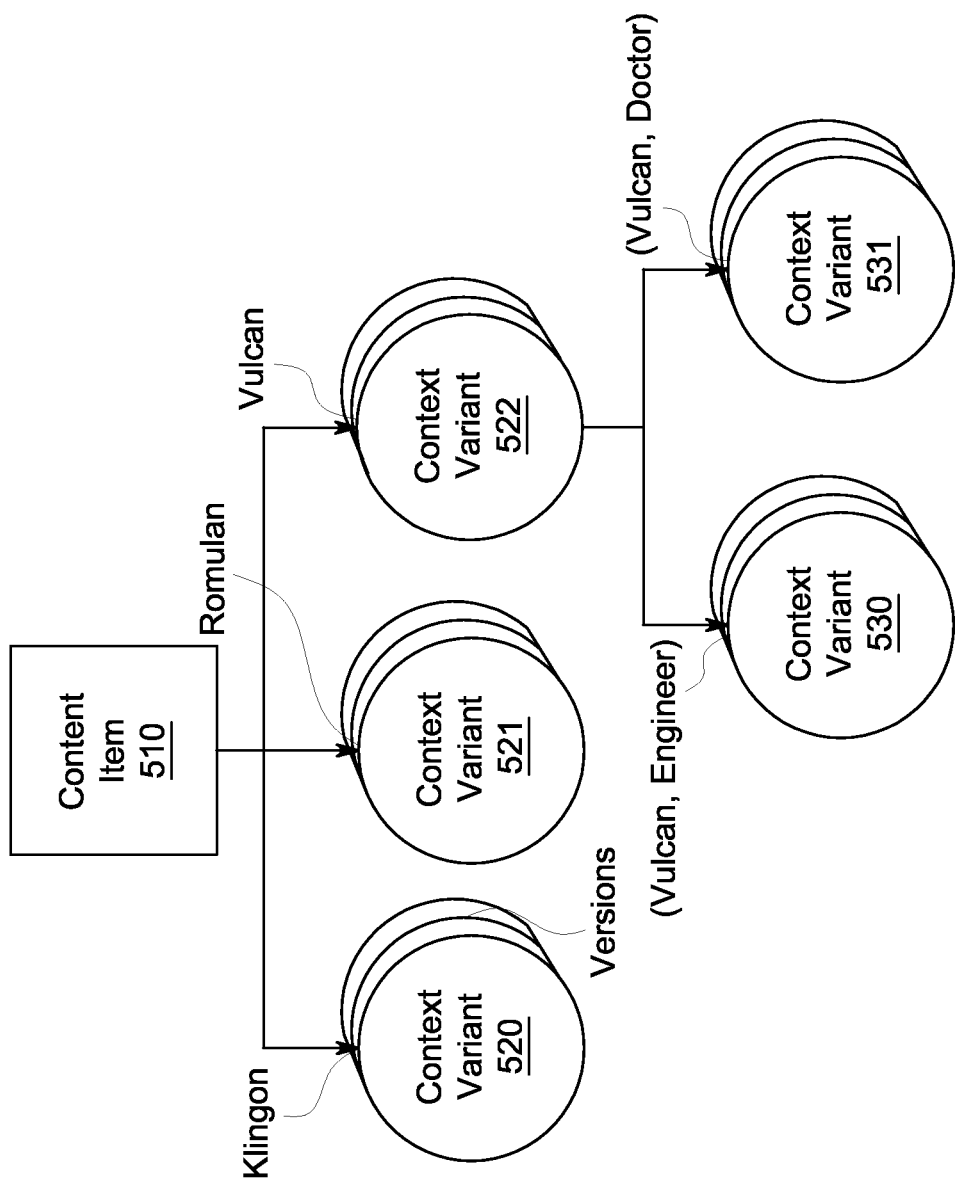
FIG. 5 shows an example of a root content item with one or more content variants and one or more context variants.

As shown in the example of FIG. 5, a root content item 510 has one or more content variants 520-522. Each content variant 520-522 may be associated with one or more context variants 530-531.

Figure 6:
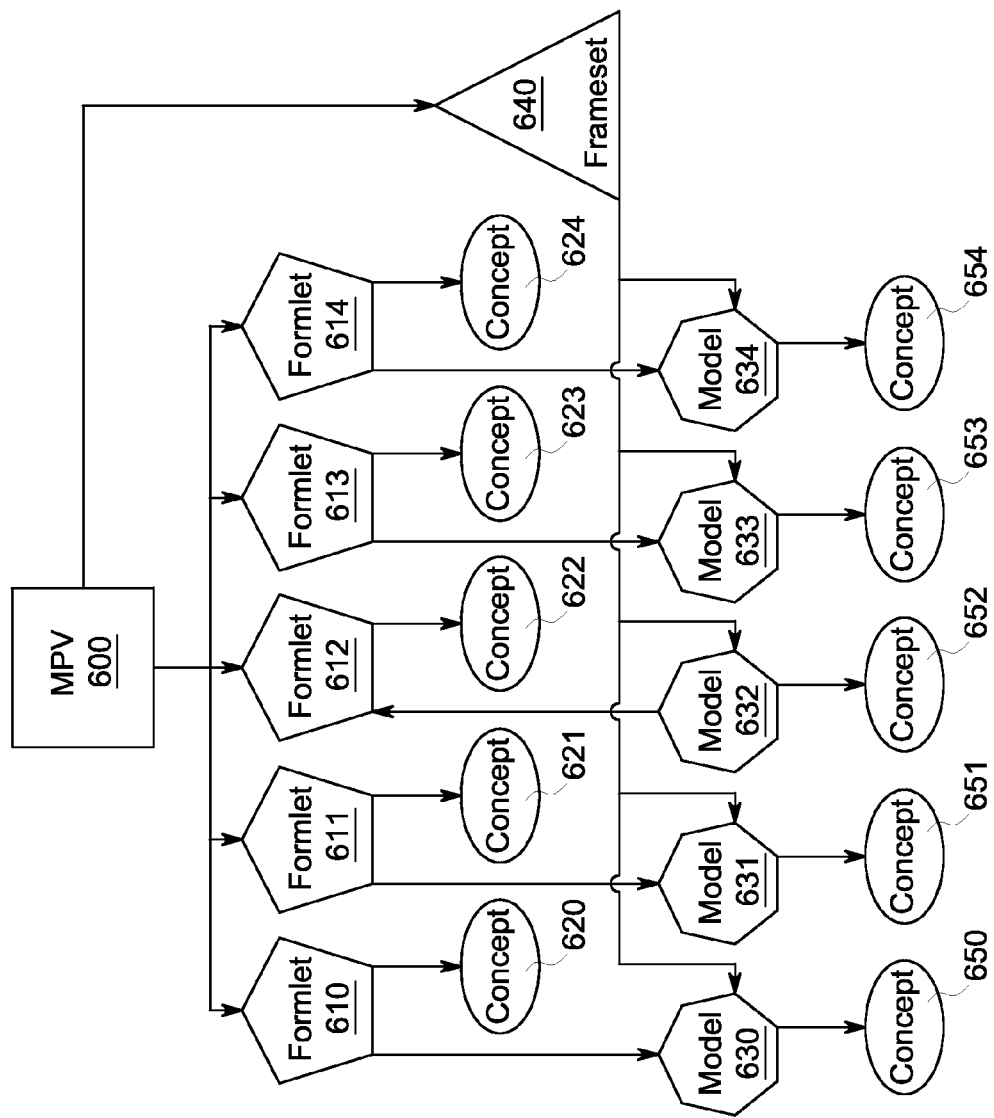
FIG. 6 provides an example multi-patient view made up of a plurality of formlets and a frameset.

FIG. 6 provides an example multi-patient view (MPV) 600 made up of a plurality of formlets 610-614 and a frameset 640. Each formlet 610-614 corresponds to a concept 620-624 and a model 630-634. The frameset 640 is also associated with each model 630-634, and each model 630-634 is associated with a concept 650-654, for example.

In certain examples, content may be stored in multiple content stores. For example, content may be stored in an ECIS database, an XDS repository, a third-party system, etc. Content documents in storage may be identified by a URI that specifies the content store and the key of that item in that content store. A content directory including the content metadata may be searched to obtain the URI for retrieval of the content item. A content type manager may specialize the search, storage, and/or retrieval of items of that content type, for example.

A content item in the content directory is keyed via a UUID for the item. That UUID is not necessarily part of the uniform resource indicator (URI) that defines the storage location.

In certain examples, content items may be organized as a content type. A content type is a set of content items that are defined and managed using common definitions and methodologies (e.g., terminology, clinical element models, frameset definitions, etc.). Content types may have different behaviors, states, lifecycles, etc. Each content type may be managed by a specific content type manager, which is treated as a plug-in to a clinical knowledge platform and/or associated clinical information system, for example. Content types may be added by creating a new content type manager, for example.

Content type managers may interact with a content management framework by implementing a set of event handlers (e.g., package, deploy, retrieve, etc.). "Generic" content types (e.g., content types with no special behavior) may use a default content type manager. An owner of a content type is responsible for implementing an associated content type manager, for example.

In certain examples, during authoring (that is, before deployment), dependencies exist between content items. At runtime (that is, after deployment), dependencies exist between deployed forms of context variants. Dependents that exist during authoring may or may not continue after deployment. For example, terminology description and pick-list resolution are translations during loading and retrieving, not dependencies per se.

In certain examples, at runtime, dependencies are between deployed forms of context variants, not the context variants themselves. The deployed form of a context variant is a "content frame". At deployment time, it may be necessary to guarantee that the packages (e.g., terminology) that a package depends on are also deployed. Terminology dependencies may be inferred from terminology relationships and mappings and do not need to be explicitly tracked.

In certain examples, a content based system provides a capability to distribute content and content updates to external instances (e.g., test systems, quality assurance systems, customer installations, content patches (SPRS), etc.). An example distribution system provides a capability to distribute content items and associated dependent content items and/or insure that those content items already exist in the target system. For example, an FDL content item must have access to the clinical element types it references in order to process a frame query. The example distribution system may also facilitate an undo or reversal of installed content items that generate issues. Content may be distributed as large sets of items (e.g., during installation) and/or as individual items (e.g., bug fixes), for example.

Applications written to leverage the systems, platforms, protocols, and methodologies described above make frequent requests for content and data. Given the allowable variance in types and/or context of content, a cache query may often incorrectly result in a determination that memory (e.g., a clinical data repository or other main memory or storage) is to be queried for the requested content. Certain examples help improve cache hit success rate by using a split cache that caches separately 1) the data required to determine which item(s) to retrieve and 2) the item(s) themselves.

A service that uses a cache to return data typically receives an identifier, checks to see if the identifier is in the cache and, if found, returns the data from the cache. If the identifier is not found in the cache, the service retrieves the data from another service, file system, or database. The service then stores the data in the cache and returns the data. The next time the data is needed, a call to another service is not necessary until, perhaps, the data is replaced in the cache.

For the cache retrieval process to work correctly, each identifier should uniquely identify the items in the cache. If the data in the cache can be represented by more than one identifier, then the cache either needs to store the data in duplicate under each identifier or store all the identifiers for each data item, for example.

In more complicated cases, the service takes multiple inputs to determine which data to return. In those cases, the data should be stored in the cache with a composite key formed of all the inputs. In the "simple" cache above, a cache hit is returned if all the inputs are the same. In situations where there are a large number of possible inputs that might resolve to only a few number of data items, a simple cache may not be sufficient.

Certain examples provide a solution for a situation in which a service involves a cache and takes multiple inputs, but, much of the time, unique inputs may resolve to the same data item. In this instance, multiple inputs are obtained from the caller/requester (e.g., the requesting application or function within the application). The service takes the inputs and uses them to query a database and/or other storage and then applies some business logic to determine which data to return. After determining which data or content is most appropriate, the service returns the data to the requestor. Thus, certain examples address a difficulty arising from situations in which request inputs often differ from one call to the next, but, quite often, the data returned is the same. The traditional approach of using the inputs as a composite key for the cache will almost always result in a cache miss even when the cache holds the data the user needs.

Certain examples provide a "smart" cache that is split or divided in two segments, logically and/or physically. One segment caches the content being requested. The other segment caches the metadata information used to determine which content to return. A content query service uses input data to request metadata information to determine which content to return. The service then executes business logic with respect to that metadata to determine which content is associated with the metadata. The service then checks the content cache for the content to return. By splitting the cache, the number of cache hits is increased. It is also possible to have cache hits even when non-identical metadata is passed into subsequent calls to the service.

In certain examples, the split cache is not a multi-level cache, as the two cache segments are on the same level.

In certain examples, the cache or content query service is divided into to two internal calls, with a cache serving each call. A first or "main" service takes in an identifier to be retrieved along with desired metadata information. The main service then makes a first internal call requesting existing metadata associated with the given identifier. That metadata can then be cached. The main service then examines that metadata to determine which version of content to return. The main service then executes or triggers a second internal call to retrieve a specific content version. If the content version is already in the content cache, the item can be returned from the cache. Otherwise, the content version is retrieved from a memory and/or other storage.

Thus, certain examples provide systems and methods to help provide more cache hits than traditional cache strategies and result in improved performance. If a cache miss occurs, the service makes one call over the bus or network to retrieve the requested content outside the cache.

Figure 7:
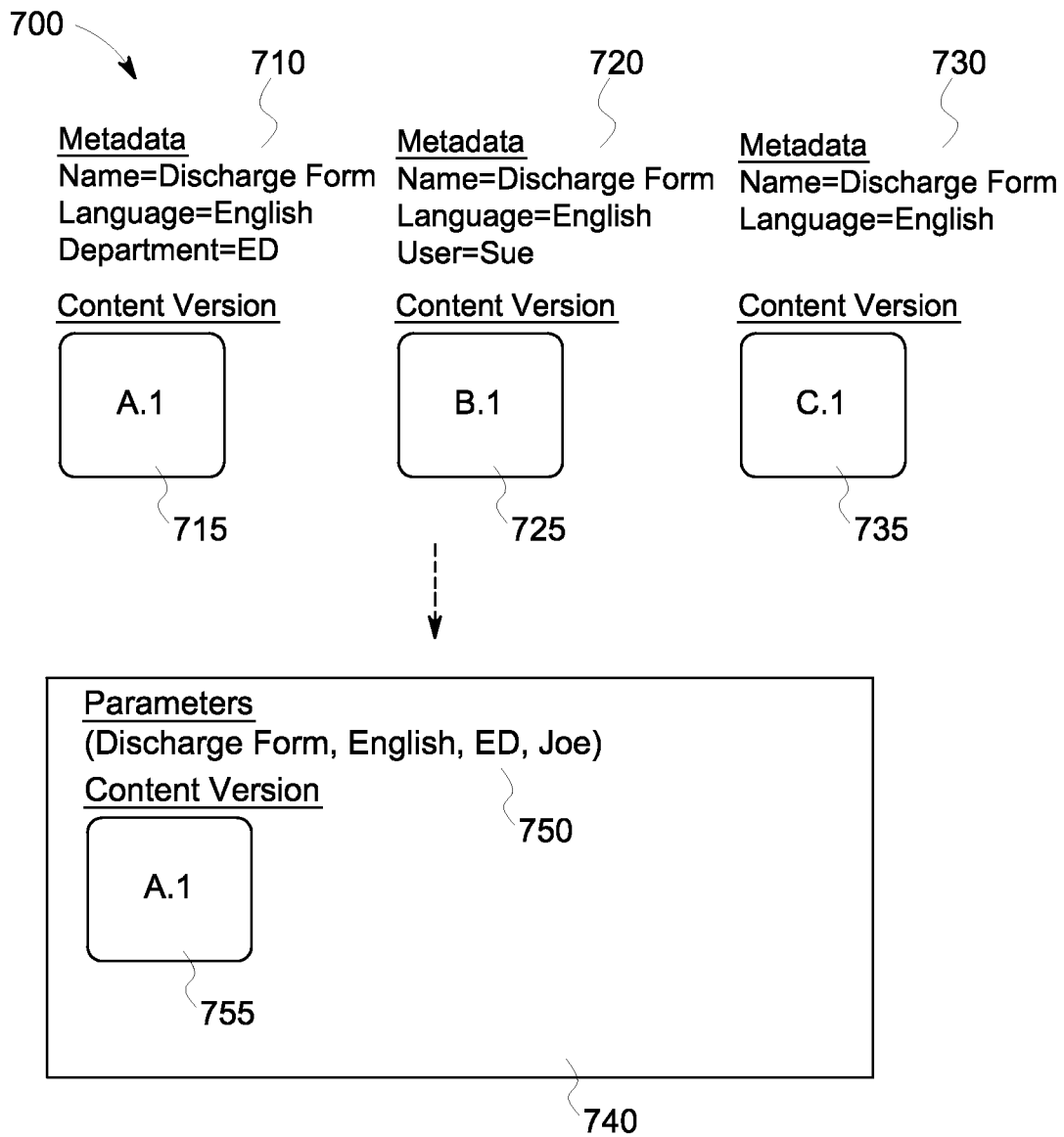
FIG. 7 illustrates an example of how a traditional cache might attempt to cache content with metadata.

FIG. 7 illustrates an example of how a traditional cache might attempt to cache content with metadata. As demonstrated in FIG. 7, an example system 700 includes three discharge forms. The discharge forms include a first discharge form having a first metadata 710 and a content version A.1 715. Metadata 710 includes one or more parameters/identifiers such as form name, language, department, etc. For example, the metadata name may be "discharge form." The language may be English, for example. The associated department may be the emergency department (ED), for example. Other metadata items may include user, etc. In addition to metadata 710 and content version 715, forms may include metadata 720 and content version B.1 725 and metadata 730 and content version C.1 735.

In the example of FIG. 7, a call or request (e.g., automatically from an application, from a user via an application interface, etc.) for content first searches a cache 740 for the requested content. For example, a call to getContent (Discharge Form, English, ED, Joe) queries the cache 740 to return content version A.1 755 with parameters (Discharge Form, English, ED, Joe) 750 found in the cache 740. A call to getContent (Discharge Form, English, ED, Bob) will also return content version A.1.

Since the parameters are different between the first content request, having a user of "Joe", and the second content request, having a user of "Bob", the cache 740 cannot return A.1 because the cache 740 does not know that the service will still return A.1. If parameters (Discharge Form, English, ED, Sue) were passed in, the cache 740 would return content version B.1 because the form with User=Sue is a better match.

Figure 8:
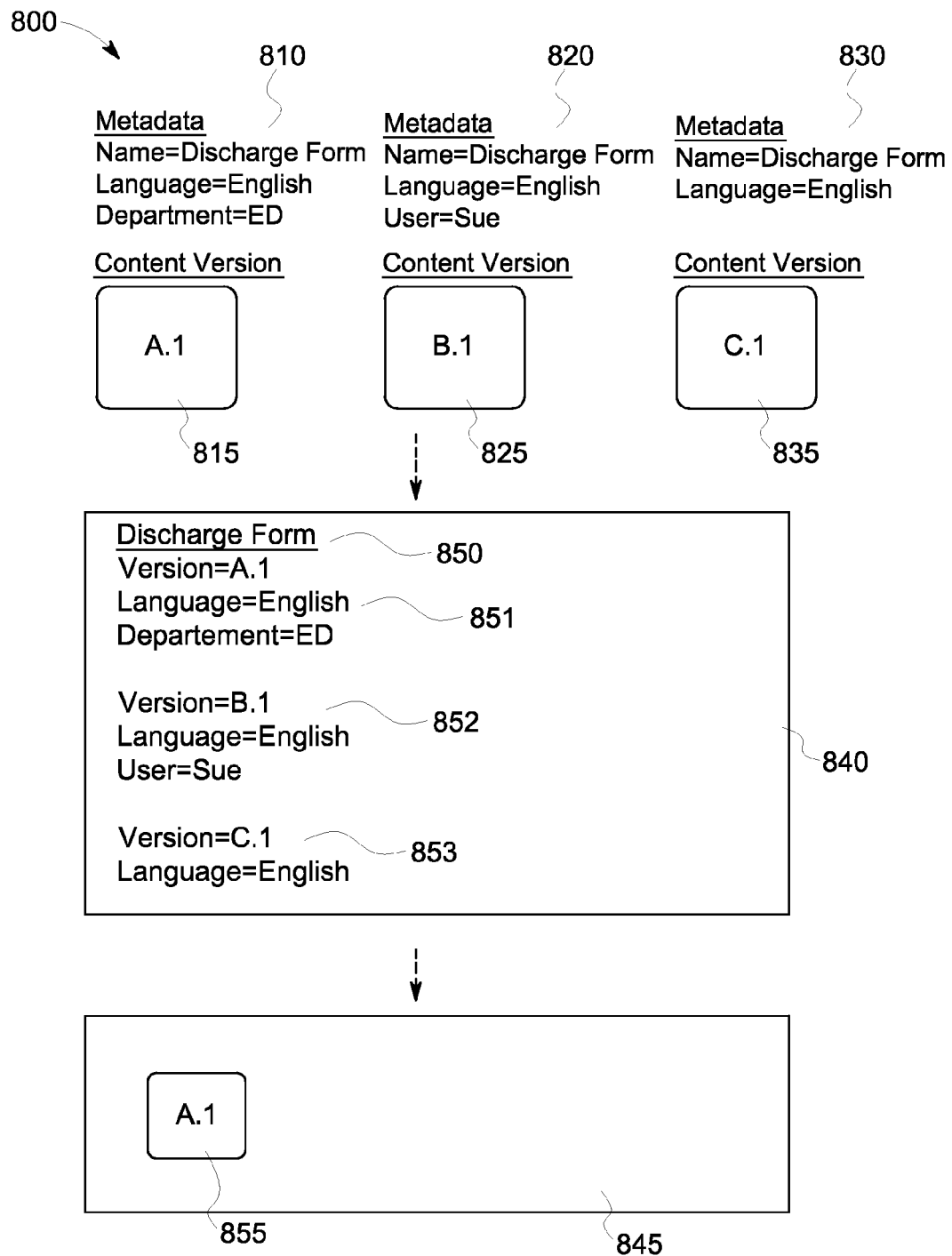
FIG. 8 illustrates an example two-phase cache approach for caching content with metadata.

FIG. 8 illustrates an example two-phase cache approach for caching content with metadata. As demonstrated in FIG. 8, an example system 800 includes three discharge forms. The discharge forms include a first discharge form having a first metadata 810 and a content version A.1 815. Metadata 810 includes one or more parameters/identifiers such as form name, language, department, etc. For example, the metadata name may be "discharge form." The language may be English, for example. The associated department may be the emergency department (ED), for example. Other metadata items may include user, etc. In addition to metadata 810 and content version 815, forms may include metadata 820 and content version B.1 825 and metadata 830 and content version C.1 835.

In the example of FIG. 8, a call or request (e.g., automatically from an application, from a user via an application interface, etc.) for content first searches a cache 840 for the requested content. For example, a call to getContent (Discharge Form, English, ED, Joe) queries the cache to return content version A.1

A split cache 840, 845 can store the metadata 810, 820, 830 of all of the discharge form content items in the metadata cache. For example, a metadata portion 840 of the split cache (e.g., logically and/or physically split cache) includes discharge form metadata 880 including metadata 851 for content version A.1, metadata 852 for content version B.1, and metadata 853 for content version C.1. Then, the discharge forms themselves can be stored in a separate content cache 845. For example, a request for content A.1 can match and retrieve the metadata 851 from the metadata cache 840 and the content version itself A.1. 855 from a content cache 845.

Thus, a call to getContent (Discharge form, English, ED, Bob) uses metadata from the metadata cache 840 to determine that A.1 851 is the correct version. Then, the call returns content version A.1 directly from the content cache 845. A call to getContent (Discharge Form, English, ED, Sue) uses the metadata from the metadata cache 840 to determine that B.2 852 is the correct version. Then, the call results in a content cache 845 miss and go to a data store to return B.1, since only A.1 855 is resident in the content cache 845 during the request.

Figure 9:
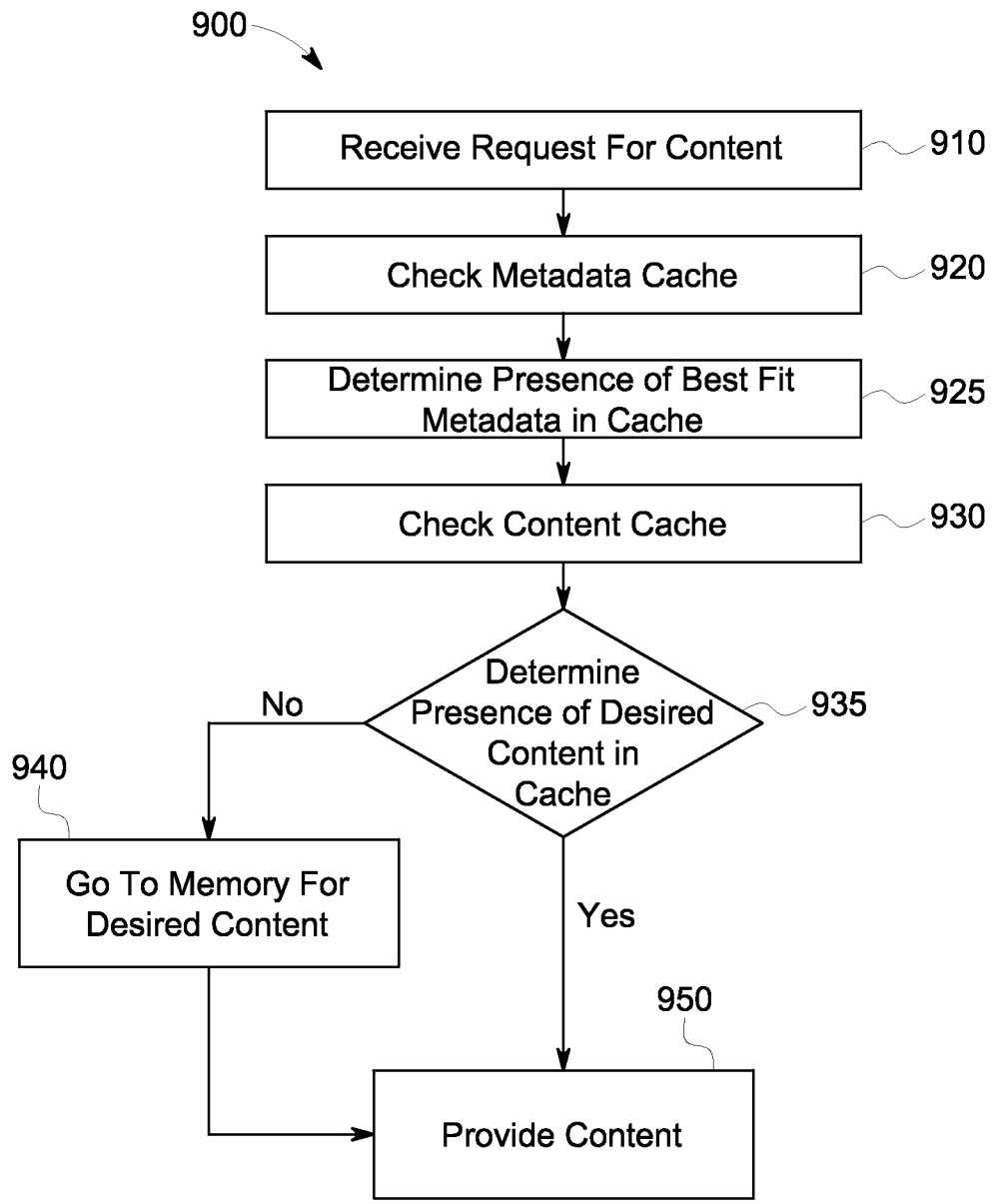
FIG. 9 depicts a flow diagram of an example method for split cache querying.

FIG. 9 depicts a flow diagram 900 of an example method for split cache querying. At block 910, a request for content is received. The content includes one or more parameters in addition to a content item (e.g., a type, role, location, etc., associated with a form). At block 920, a metadata cache is checked for the requested content. At block 925, a presence of a best fit metadata in the metadata cache is determined. For example, the one or more parameters associated with the content item are compared to metadata in the metadata cache related to content items. Metadata most closely matching (or, in some examples, exactly matching) the parameter(s) is identified to determine which content item should be retrieved.

At block 930, a content cache is checked for the requested content item. At block 935, a presence of the desired content item in the content cache is determined. If the content item is not present in the content cache, then, at block 940, another memory (e.g., a content storage, main memory, etc.) is accessed to retrieve the content item, and, at block 950, the content is provided. If the content item is present in the content cache, then, at block 950, the content is provided. The content item may be displayed, shared, transmitted, stored, etc., to a user, an application, etc.

Figure 10:
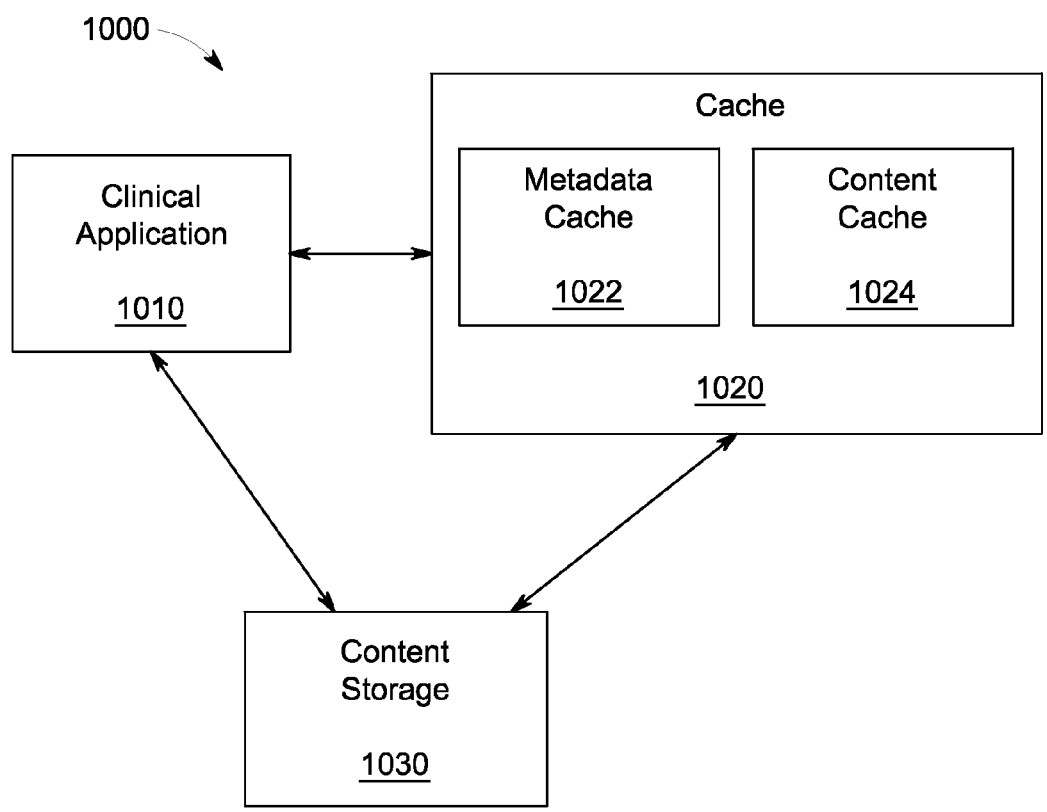
FIG. 10 illustrates an example clinical system in which a split cache may operate.

FIG. 10 illustrates an example clinical system 1000 in which a split cache may operate. The system 1000 includes a clinical application 1010, a cache 1020, and a content storage 1030. The cache 1020 is divided (e.g., physically and/or logically) into a metadata cache 1022 and a content cache 1024. Components of the system 1000 can be implemented together and/or separately in hardware, firmware, software, and/or a combination thereof. As discussed above, a request or call for content from the application 1010 results first in a query of the metadata cache 1022, followed by a query of the content cache 1024. Items not found in the cache 1020 may be retrieved from the content storage 1030.

While an example manner of implementing systems and methods have been illustrated in the figures, one or more of the elements, processes and/or devices illustrated in the figures may be combined, divided, re-arranged, omitted, eliminated and/or implemented in any other way. Further, one or more components and/or systems may be implemented by hardware, software, firmware and/or any combination of hardware, software and/or firmware. Thus, for example, any of the example components and/or systems may be implemented by one or more circuit(s), programmable processor(s), application specific integrated circuit(s) (ASIC(s)), programmable logic device(s) (PLD(s)) and/or field programmable logic device(s) (FPLD(s)), etc. When any of the appended claims are read to cover a purely software and/or firmware implementation, at least one of the example components and/or systems are hereby expressly defined to include a tangible medium such as a memory, DVD, Blu-ray, CD, etc., storing the software and/or firmware. Further still, any of the example systems may include one or more elements, processes and/or devices in addition to, or instead of, those illustrated in the figures, and/or may include more than one of any or all of the illustrated elements, processes and devices.

The flow diagrams depicted in the figures (e.g., FIG. 9) are representative of machine readable instructions that can be executed to implement example processes and/or systems described herein. The example processes may be performed using a processor, a controller and/or any other suitable processing device. For example, the example processes may be implemented in coded instructions stored on a tangible medium such as a flash memory, a read-only memory (ROM) and/or random-access memory (RAM) associated with a processor (e.g., the example processor 1112 discussed below in connection with FIG. 11). Alternatively, some or all of the example processes may be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes may be implemented manually or as any combination(s) of any of the foregoing techniques, for example, any combination of firmware, software, discrete logic and/or hardware. Further, although the example processes are described with reference to the figures, other methods of implementing the processes of may be employed. For example, the order of execution of the blocks may be changed, and/or some of the blocks described may be changed, eliminated, sub-divided, or combined. Additionally, any or all of the example processes of may be performed sequentially and/or in parallel by, for example, separate processing threads, processors, devices, discrete logic, circuits, etc.

Figure 11:
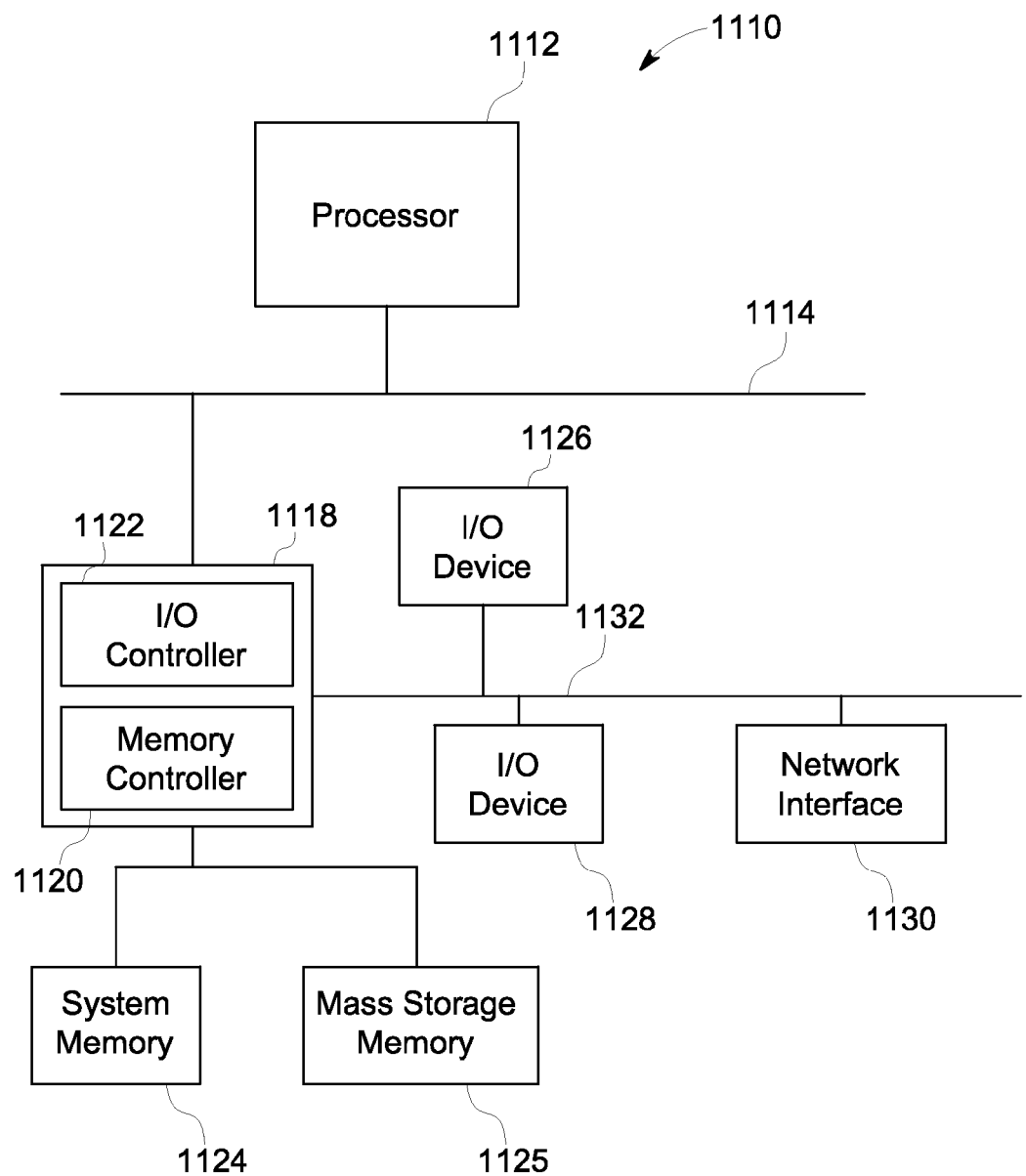
FIG. 11 illustrates a block diagram of an example processor system that can be used to implement the apparatus and methods described herein.

FIG. 11 is a block diagram of an example processor system 1110 that may be used to implement the apparatus and methods described herein. As shown in FIG. 11, the processor system 1110 includes a processor 1112 that is coupled to an interconnection bus 1114. The processor 1112 may be any suitable processor, processing unit or microprocessor. Although not shown in FIG. 11, the system 1110 may be a multi-processor system and, thus, may include one or more additional processors that are identical or similar to the processor 1112 and that are communicatively coupled to the interconnection bus 1114.

The processor 1112 of FIG. 11 is coupled to a chipset 1118, which includes a memory controller 1120 and an input/output (I/O) controller 1122. As is well known, a chipset typically provides I/O and memory management functions as well as a plurality of general purpose and/or special purpose registers, timers, etc. that are accessible or used by one or more processors coupled to the chipset 1118. The memory controller 1120 performs functions that enable the processor 1112 (or processors if there are multiple processors) to access a system memory 1124 and a mass storage memory 1125.

The system memory 1124 may include any desired type of volatile and/or non-volatile memory such as, for example, static random access memory (SRAM), dynamic random access memory (DRAM), flash memory, read-only memory (ROM), etc. The mass storage memory 1125 may include any desired type of mass storage device including hard disk drives, optical drives, tape storage devices, etc.

The I/O controller 1122 performs functions that enable the processor 1112 to communicate with peripheral input/output (I/O) devices 1126 and 1128 and a network interface 1130 via an I/O bus 1132. The I/O devices 1126 and 1128 may be any desired type of I/O device such as, for example, a keyboard, a video display or monitor, a mouse, etc. The network interface 1130 may be, for example, an Ethernet device, an asynchronous transfer mode (ATM) device, an 802.11 device, a DSL modem, a cable modem, a cellular modem, etc. that enables the processor system 1110 to communicate with another processor system.

While the memory controller 1120 and the I/O controller 1122 are depicted in FIG. 11 as separate blocks within the chipset 118, the functions performed by these blocks may be integrated within a single semiconductor circuit or may be implemented using two or more separate integrated circuits.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Although certain methods, apparatus, and articles of manufacture have been described herein, the scope of coverage of this patent is not limited thereto. To the contrary, this patent covers all methods, apparatus, and articles of manufacture fairly falling within the scope of the appended claims either literally or under the doctrine of equivalents.

The invention claimed is:

1. A clinical split cache system for retrieval of varying clinical content, the system comprising:
   an input to include a request for a content item and one or more parameters associated with the content item;
   a metadata cache to store one or more sets of metadata representing parameters associated with one or more content items, the one or more sets of metadata in the metadata cache to be used to identify and distinguish between versions of one or more content items with respect to the request;
   a content cache to store one or more content items, the one or more content items searchable based on associated metadata, wherein the metadata cache and the content cache are to facilitate the request by first querying the metadata cache and then querying the content cache based on a result of the metadata cache query; and
   an output of the requested content item, wherein the request is divided into two internal calls for the requested content item, a first call requesting metadata associated with the content item and a second call to request a version of the requested content item based on the metadata and an identifier associated with the content item.

2. The system of claim 1, wherein metadata not found in the metadata cache as a result of the first call is to be retrieved from a memory and cached in the metadata cache, and wherein the requested content item not found in the content cache as a result of the second call is to be retrieved from a memory and cached in the content cache.

3. The system of claim 1, wherein the first call requesting metadata associated with the content item is to be examined to determine a version of the requested content item to be retrieved, and wherein the second call is to request the version of the requested content item based on the metadata.

4. The system of claim 3, wherein the system further comprises a processor to apply business logic to the metadata to determine the version of the content item to be returned in response to the request.

5. The system of claim 1, wherein the metadata cache and the content cache are arranged as part of the same cache and sit on the same cache level.

6. The system of claim 1, wherein the one or more parameters associated with the content item comprise a plurality of parameters to be compared with a plurality of metadata.

7. The system of claim 6, wherein the plurality of parameters comprises a content type and at least one of a language, a user, and a location.

8. A tangible computer-readable storage device or storage disc including a set of instructions, which when executed by a processor, implement a clinical split cache system for retrieval of varying clinical content, the system comprising:
   an input to include a request for a content item and one or more parameters associated with the content item;
   a metadata cache to store one or more sets of metadata representing parameters associated with one or more content items, the one or more sets of metadata in the metadata cache to be used to identify and distinguish between versions of one or more content items with respect to the request;
   a content cache to store one or more content items, the one or more content items searchable based on associated metadata, wherein the metadata cache and the content cache are to facilitate the request by first querying the metadata cache and then querying the content cache based on a result of the metadata cache query; and
   an output of the requested content item, wherein the request is divided into two internal calls for the requested content item, a first call requesting metadata associated with the content item and a second call to request a version of the requested content item based on the metadata and an identifier associated with the content item.

9. The tangible computer-readable storage device or strage disc of claim 8, wherein metadata not found in the metadata cache as a result of the first call is to be retrieved from a memory and cached in the metadata cache, and wherein the requested content item not found in the content cache as a result of the second call is to be retrieved from a memory and cached in the content cache.

10. The tangible computer-readable storage device or storage disc of claim 8, wherein the first call requesting metadata associated with the content item is to be examined to determine a version of the requested content item to be retrieved, and wherein the second call is to request the version of the requested content item based on the metadata.

11. The tangible computer-readable storage device or storage disc of claim 10, further comprising a processor to apply business logic to the metadata to determine the version of the content item to be returned in response to the request.

12. The tangible computer-readable storage device or storage disc of claim 8, wherein the metadata cache and the content cache are arranged as part of the same cache and sit on the same cache level.

13. The tangible computer-readable storage device or storage disc of claim 8, wherein the one or more parameters associated with the content item comprise a plurality of parameters to be compared with a plurality of metadata.

14. The tangible computer-readable storage device or storage disc of claim 13, wherein the plurality of parameters comprises a content type and at least one of a language, a user, and a location.

15. A method of retrieving varying clinical content, the method comprising:
   receiving a request for a content item and one or more parameters associated with the content item;
   querying a metadata cache based on the one or more parameters associated with the content item and a content item identifier to identify metadata associated with the requested content item, the metadata cache storing one or more sets of metadata representing parameters associated with one or more content items, the one or more sets of metadata in the metadata cache to be used to identify and distinguish between versions of one or more content items with respect to the request;

querying a content cache using the content item identifier and the metadata associated with the request content item, the content cache to store one or more content items, the one or more content items searchable based on associated metadata, wherein the metadata cache and the content cache are to facilitate the request by first querying the metadata cache and then querying the content cache based on a result of the metadata cache query; and providing an output of the requested content item, wherein the request is divided into two internal calls for the requested content item, a first call requesting metadata associated with the content item and a second call to request a version of the requested content item based on the metadata and an identifier associated with the content item.

16. The method of claim 15, wherein the first call requesting metadata associated with the content item is to be examined to determine a version of the requested content item to be retrieved, and wherein the second call is to request the version of the requested content item based on the metadata.

17. The method of claim 16, wherein the system further comprises a processor to apply business logic to the metadata to determine the version of the content item to be returned in response to the request.

18. The method of claim 15, wherein the metadata cache and the content cache are arranged as part of the same cache and sit on the same cache level.

19. The method of claim 15, wherein the one or more parameters associated with the content item comprise a plurality of parameters to be compared with a plurality of metadata.

20. The method of claim 19, wherein the plurality of parameters comprises a content type and at least one of a language, a user, and a location.

* * * * *